(12) United States Patent
Wiktor (10) Patent No.: US 6,232,129 B1
(45) Date of Patent: May 15, 2001

(54) PIEZOELECTRIC PIPETTING DEVICE

(76) Inventor: Peter Wiktor, 3226 NE. 87th St., Seattle, WA (US) 98115

( * ) Notice: Subject to any disclaimer, the term of this patent is extended or adjusted under 35 U.S.C. 154(b) by 0 days.

(21) Appl. No.: 09/243,018

(22) Filed: Feb. 3, 1999

(51) Int. Cl.[7] ............................... B01L 3/02; B01L 11/00
(52) U.S. Cl. .................... 436/180; 422/100; 422/103; 73/864.02; 73/864.24
(58) Field of Search ................. 422/100, 103; 73/864.02, 864.24; 436/180

(56) References Cited

U.S. PATENT DOCUMENTS

| | | | |
|---|---|---|---|
| 2,512,743 | 6/1950 | Hansell | 91/18 |
| 3,613,952 | 10/1971 | Gilmont | 222/43 |
| 3,766,785 | 10/1973 | Smernoff | 73/425.6 |
| 3,827,305 | 8/1974 | Gilson | 73/425 |
| 3,840,758 | 10/1974 | Zoltan | 310/8.1 |
| 3,991,617 | 11/1976 | Marteau d'Autry | 73/425.4 P |
| 4,432,699 | 2/1984 | Beckman et al. | 417/63 |
| 4,905,526 | * 3/1990 | Magnussen, Jr. et al. | 73/864.18 |
| 5,045,286 | * 9/1991 | Kitajima et al. | 422/100 |
| 5,236,473 | * 8/1993 | Kraus et al. | 95/30 |
| 5,241,363 | * 8/1993 | Garner | 356/326 |
| 5,518,179 | 5/1996 | Humberstone et al. | 239/102.2 |
| 5,622,897 | 4/1997 | Hayes | 438/21 |
| 5,741,554 | 4/1998 | Tisone | 427/424 |
| 5,743,960 | 4/1998 | Tisone | 118/683 |
| 5,785,926 | * 7/1998 | Seubert et al. | 422/100 |
| 5,807,522 | 9/1998 | Brown et al. | 422/50 |
| 5,855,851 | * 1/1999 | Matsubara et al. | 422/100 |
| 5,916,524 | * 6/1999 | Tisone | 422/100 |
| 5,927,547 | * 7/1999 | Papen et al. | 222/57 |
| 5,958,342 | * 9/1999 | Gamble et al. | 422/100 |
| 6,063,339 | * 5/2000 | Tisone et al. | 422/67 |
| 6,083,762 | * 7/2000 | Ppen et al. | 436/180 |

OTHER PUBLICATIONS

*Robotic Sample Processors* brochure, Tecan AG, Hombrechitkon, Switzerland—date unknown.
*Microlab Automated PipettingSystem*, Hamilton Company, Reno, NV (Feb. 1996?).
Carvo Scientific Instruments, Inc. brochure, Sunnyvale, CA (date unknown).
*HYDRA Microdispensers*, Robbins Scientific, Sunnyvale, CA (date unknown).
*BioRobot 9600* Product Brochure, Qiagen, Inc., Valencia, CA (date unknown).
*Quadra* 96 Product Information, Tomtec, Orange CT, (date unknown).
*PixSys 3500* Product Brochure, Caresian Technologies, Inc., Irvine, CA (date unknown).
*MultiGrid* Product Information, GeneMachines, Menlo Park, CA (date unknown).
*MultiProbe Robotic Liquid Handling Systems*, Packard InstrumentCo., Meriden, CT (date unknown).
*Microdosing in the picoliter range with piezo technology*, Microdrop mbH, Norderstedt, Germany (date unknown).

(List continued on next page.)

Primary Examiner—Jill Warden
Assistant Examiner—Brian R. Gordon
(74) *Attorney, Agent, or Firm*—Graybeal Jackson Haley LLP (57) ABSTRACT

A piezoelectric actuated device for acquiring and dispensing fluid samples is described. Fluid samples are acquired or drawn up into the device by dipping the tip into a fluid and applying an alternating current electrical signal to the piezoelectric element. Removing the tip from the fluid and applying another electrical signal causes drops of fluid to be ejected for non-contact dispensing. The device optionally incorporates a second piezoelectric element functioning as a sensor to detect if it is empty, plugged or working properly. An optional heater, temperature sensor and feedback circuitry regulate the temperature of the device.

22 Claims, 8 Drawing Sheets

OTHER PUBLICATIONS

*Microejection Pump Technical Data*, GeSiM mbH, Dresen, Germany, Jun. 1996.
*Monolithic Termocouple Amplifier with Cold Junction Compensation* Data Sheet, Analog Devices, Norwood, MA (date unknown).

*Micromachined Transducers Sourcebook*, Gregory T.A. Kovacs, McGraw–Hill, p. 842.
Piezoelectric Actuated Reagent Dispenser with Integral Pressure Sensor Lauren R. Sjoboen, Thesis, 1977, p. 3.
*Multimek 96* Product Brochure, Beckman Coulter, 1998.

* cited by examiner

PIEZOELECTRIC PIPETTING DEVICE

BACKGROUND OF THE INVENTION

The present invention relates to a piezoelectric actuated device for manually or automatically transferring very small volumes of fluid. Transferring fluids from one container to another is one of the most common tasks performed in a typical chemical or biological laboratory. For example, various chemicals from different containers may have to be mixed together and then the mixture may have to be divided out equally or 'aliquoted' into other containers or onto microscope slides or some other substrates. Currently transferring of fluids is done either by hand using manual pipettors or automatically using an automated robotic pipetting instruments. Motivated by the high costs of chemical reagents there is a trend in chemical and biological laboratories to perform experiments using smaller and smaller fluid samples.

Prior to the 1990's fluid transfer was done in laboratories by hand using glass tubes called pipettes. Samples were aspirated by sucking on the end of the pipette by mouth like a straw and then sealing the end with a finger. Fluid samples were then dispensed or aliquoted by briefly unsealing and then resealing the pipette with the finger allowing a small volume of fluid to flow out. This method required a fair amount of dexterity and had some serious drawbacks in terms of ergonomics, precision and health risks. During the same time period glass capillaries were also used for transferring smaller volumes of fluid with greater precision. These techniques for manually transferring fluid samples were made obsolete in the early 1990's by the introduction of the manual pipette as described, for example, in U.S. Pat. Nos. 3,613,952, 3,766,785, 3,827,305 and 3,991,617, with ejectable, disposable plastic tips. Currently the manual pipette is a ubiquitous and indispensable tool for transferring fluid samples in the modern laboratory.

Although manual pipetting is a big improvement over earlier techniques it is tedious for the human operator and can cause repetitive motion injuries as well as being prone to human error. Currently, a great variety of automated pipetting instruments are commercially available which address these specific drawbacks. These instruments, as advanced by Tecan AG of Hombrechtikon Switzerland, typically use a Cartesian X,Y,Z robot to move a pipetting head among various aspirating, dispensing and washing stations. The various types of instruments currently available differ mainly in the mechanisms used to acquire and then dispense fluid samples. The most common mechanism for fluid transfer is the syringe pump as used in instruments manufactured by Tecan, Hamilton Company, Cavro Scientific Instruments, Robbins Scientific, Qiagen and Tomtec among others. In most cases the syringe pumps and pipette tips are connected via long flexible tubing, however, in the instruments supplied by Tomtec and Robbins Scientific the syringe pumps are mounted directly to the back of the pipette tips. The smallest volume that can be accurately transferred using syringe pumps is approximately 0.1 microliters. U.S. Pat. Nos. 5,743,960 and 5,741,554 describe an instrument which combines a syringe pump with a solenoid valve allowing drops as small as 0.1 microliters to be ejected onto a substrate for non-contact printing or arraying applications. By contrast, the drops that are dispensed using the present invention are a thousand times smaller.

Another method for transferring small volumes of fluid for arraying applications is the use of pins as described in U.S. Pat. No. 5,807,522. Instruments using pins for fluid transfer are used by Synteni, among other companies, to generate DNA arrays and are commercially available, for example, from BioRobotics and GeneMachines. Using pins is a simple, robust and practical means for fluid transfer but it suffers from some limitations. First of all it is slow. The pins have to stop at each spot and then wait for over a second for capillary action to transfer the fluid onto the substrate. By contract, the piezoelectric based dispensing of the present invention is almost a thousand times faster. Pin based fluid transfer is sensitive to the wetting properties of the substrate. Also it can damage some substrates like Nylon membranes for example. These are not concerns for the piezoelectric dispensing which is non-contact. Pins generate relatively low density, poor quality arrays with approximately 50% variability in spot size. By contrast, piezoelectric dispensers generate arrays with almost an order of magnitude higher density and better than 3% spot size variability. Finally, pins are limited to acquiring and dispensing a fixed volume of fluid. Piezoelectric dispensers have thousands of times higher dynamic range. Sub nanoliter to tens of microliter volumes can be aspirated and subsequently dispensed in volumes ranging from 100 picoliters to several microliters per second.

A number of companies including Microdrop, Packard Instruments and GeSiM, use piezoelectric fluid dispensing devices to dispense drops of fluid with volumes on the order of 100 picoliters. Originally piezoelectric dispensing technology was used for "drop-on-demand" "ink-jet" printing. These devices as described in U.S. Pat. No. 2,512,743 have a fluid filled chamber with an inlet at one end and a nozzle on the other. A piezoelectric element induces an acoustic wave in the fluid causing a drop to be ejected from the nozzle. For printing applications ink is supplied to the back end of the piezoelectric fluid dispenser from a reservoir. For fluid transfer applications fluid is drawn up through the nozzle. The instruments supplied by Microdrop, Packard Instruments and GeSiM all use syringe pumps to aspirate fluids up through the nozzle of the piezoelectric devices. Syringe pumps impose several serious limitations on current piezoelectric based pipetting instruments. It turns out that properly aspirating samples prior to dispensing is one of the most critical considerations for reliable operation of piezoelectric fluid dispensers. Syringe pumps can sometimes aspirate air bubbles and small particles that can adversely affect the dispensing characteristics. Also, variations in back pressure in the flexible tubing leading to the syringe pumps causes the drop-on-demand dispensing properties to change. Packard Instruments uses a closed loop pressure controller to actively regulate this back pressure. This system adds to the cost and complexity of the instrument. Additionally the syringe pumps themselves add significantly to the cost, size and complexity of the instrument and they limit the smallest fluid volumes that can be transferred to around 0.5 microliter. By contrast, with the present invention, volumes over 100 times smaller can be aspirated. Most importantly, aspirating is much more uniform and precise making dispensing more reliable and repeatable. In the present invention, the dispensers are opened to ambient pressure so the back pressure always remains uniform. Additionally the novel sensing technology of the present invention detects almost instantly if there is a problem with the dispensers, e.g. if they are clogged, empty or attempting to aspirate from an empty well.

The present invention provides improvements to the cylindrical piezoelectric fluid dispenser described in U.S. Pat. No. 3,840,758. These improvements enable bi-directional operation of the device, sensing of the operational state and thermal control. As a summary of some related devices. Humberstone in U.S. Pat. No. 5,518,179 describes a bi-directional device with a piezoelectric driven, thin, perforated membrane capable of drawing a fluid up through the perforations as well as dispensing fluid out through them. Beckman et al. in U.S. Pat. No. 4,432,699 describes a peristaltic piezoelectric pump with an internal load sensor. Hayes in U.S. Pat. No. 5,622,897 describes a process of manufacturing a drop-on-demand ink-jet print head having n-type and p-type thermoelectric carriers.

SUMMARY OF THE INVENTION

The invention provides a device enabling the automatic or manual transfer of small volumes of fluid from one container to another or from one container to the surface of a substrate. The device is a self contained, bi-directional pump in the sense that it can acquire fluid samples as well as dispense them. Acquiring samples in accordance with the present invention requires dipping the tip of the device into the sample fluid. Dispensing, however, does not require any contact with either a fluid or solid surface. Fluid can be dispensed one drop at a time in a "drop-on-demand" mode or continuously at frequencies from over several thousand to fifty thousand drops per second.

In accordance with further aspects of the present invention, an integral monitoring sensor detects if the piezoelectric pipette is functioning normally, is empty or if the nozzle is plugged. This type of feedback of the operational state of the device is critical for automated pipetting instruments to alert a human operator if the device requires some attention or to initiate an automated failure recovery procedure.

The characteristics of drop-on-demand ink-jet dispensers can change with temperature. In accordance with a further aspect of the present invention, a piezoelectric pipette incorporates a built in temperature regulator. This helps maintain uniform dispensing characteristics even if the ambient temperature changes. The temperature regulator can also be used to raise the temperature of the fluid being dispensed. Elevated temperatures can reduce the viscosity of fluids that are too viscous to dispense at ambient temperature.

In summary, the invention is a compact, bi-directional pump for acquiring and dispensing small volumes of fluid with a built in monitoring sensor and temperature control. The invention is suitable for automated or manual fluid transfer applications.

Accordingly, the invention provides a diffuser pump including a pipette having a capillary having a first end including a nozzle and a piezoelectric actuating element adjacent to the capillary and an alternating current voltage source coupled across the piezoelectric actuating element. With the nozzle immersed in a sample fluid and the capillary at least partially filled with a working fluid, alternating current voltage applied to the actuating element causes sample fluid to be drawn into the capillary.

The invention further provides a pipette sensing arrangement for sensing a working condition of a pipette having a capillary with an end including a nozzle, a piezoelectric actuating element adjacent to the capillary, and first electrodes for applying electrical energy across the piezoelectric actuating element. The sensing arrangement includes a piezoelectric sensing element adjacent to the capillary and second electrodes for coupling the piezoelectric sensing element to a voltage sensor.

The invention still further provides a temperature control arrangement for a pipette having a capillary having an end including a nozzle, a piezoelectric actuating element adjacent to the capillary, and actuating electrodes for applying electrical energy across the piezoelectric actuating element. The temperature control arrangement includes a current source for passing an electrical current through one of the actuating electrodes, and a temperature sensor closely adjacent the capillary for sensing the temperature of the capillary.

BRIEF DESCRIPTION OF THE DRAWINGS

The features of the present invention which are believed to be novel are set forth with particularity in the appended claims. The invention, together with further objects and advantages thereof may best be understood by making reference to the following description taken in conjunction with the accompanying drawings, in the several figures of which like reference numerals identify identical elements, and wherein:

DETAILED DESCRIPTION

Figure 1:
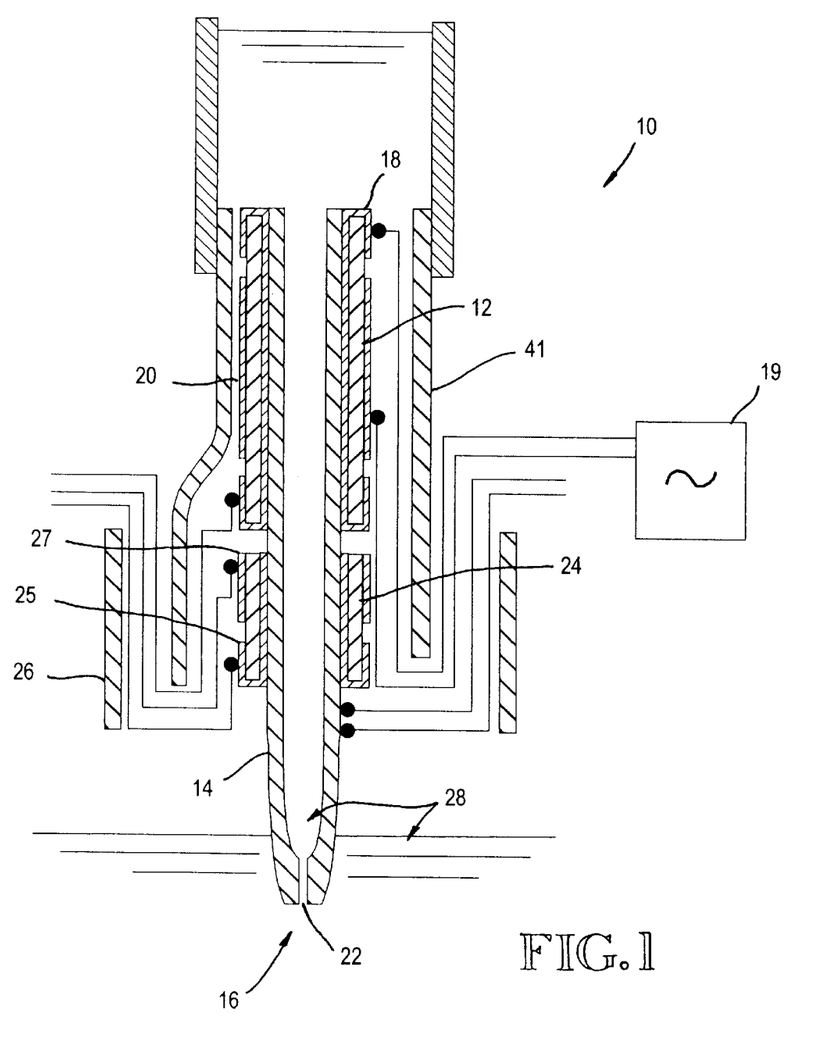
FIG. 1 is a cross-sectional view of piezoelectric pipette embodying the present invention including a sensor, temperature controller, Teflon housing and reservoir.

Referring now to FIG. 1, it illustrates a piezoelectric pipette 10 with sensor, temperature control, housing and reservoir embodying the present invention. It includes an piezoelectric actuating element 12 with a glass capillary 14 bonded concentrically on the inside. The glass capillary has a nozzle 16 formed on one end by heating and then polishing the end. Applying a voltage to the piezoelectric element 12 across an inner electrode 18 and an outer electrode 20 causes it to deflect which induces an acoustic wave in the fluid filled glass capillary 14. A drop is ejected from the nozzle if the acoustic energy is high enough to overcome surface tension at the nozzle opening 22. In accordance with the present invention, a separate sensing piezoelectric ceramic tube 24 is concentric with the glass capillary 14 and adjacent to the actuating piezoelectric element 12. These elements may also be seen in FIG. 6 with the corresponding elements having corresponding reference numerals with an "a" subscript. The piezoelectric pipette is housed in Teflon heat shrink tubing 26 and 41 as shown in FIG. 1. This housing is compact, provides mechanical protection and electrical insulation for the piezoelectric element.

Diffuser Pump Mode

With the nozzle immersed in fluid 28 as shown in FIG. 1 the device 10 operates as a diffuser pump capable of acquiring or drawing fluid samples up through the nozzle. Due to the shape of the nozzle, fluid has less resistance flowing from the sample fluid up into the glass capillary than out. Periodically deflecting the piezoelectric element by applying an alternating voltage from an alternating current source 19 to the electrodes 18 and 20 causes fluid to flow in and out of the nozzle with a net inward flow due to the lower flow resistance in this direction. Based on the diffuser pump principle it is possible to draw up fluid samples into the piezoelectric pipette when the nozzle is dipped in a fluid. The sample fluid may then be dispensed when the device operates as a drop-on-demand 'ink-jet' printer when the nozzle is removed from a fluid.

The diffuser pump works over a large range of periodic excitation voltage frequencies, amplitudes and waveforms. Pumping speed increases with frequency and amplitude. This diffuser pump mode has been demonstrated to successfully pump fluid with excitation signal frequencies ranging from 6 KHz to 25 KHz and amplitudes from 20 V to over 90 V. Pumping was demonstrated with a variety of waveform shapes including saw-tooth, square-wave and sine-wave waveforms.

Figure 2:
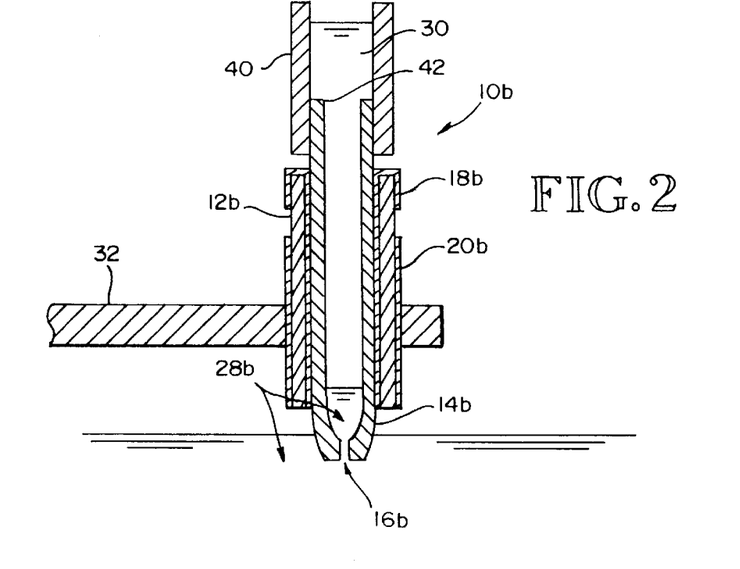
FIG. 2 is a cross-sectional view of piezoelectric pipette in a diffuser pump mode in accordance with the present invention with a reservoir attached to the back end and a mounting bracket arm for automated dipping into the sample fluid.

The glass capillary of the device must be at least partially filled with fluid to transmit acoustic energy provided by the piezoelectric element 12 to the fluid in the area of the nozzle 16 for both drop-on-demand and diffuser pump modes to function properly. This 'working' fluid does not necessarily have to be the same as the sample fluid as illustrated in FIG. 2 which shows another pipette 10b wherein corresponding elements are designated by corresponding reference numerals with a "b" subscript. Here the working fluid 30 and the sample fluid 28b are different. The working and sample fluids may be immiscible with each other allowing small fluid samples to be drawn up without diffusing the sample into the working fluid. A wide variety of fluids immiscible in, for example, water in practicing the present invention may be selected including Fluorinert manufactured by 3M, 200 Fluid manufactured by Dow Corning and paraffin. Fluorinert has a good combination of properties for many applications including low viscosity, good bio-compatibility and it does not leave a residue when dried out.

Figures 3, 4:
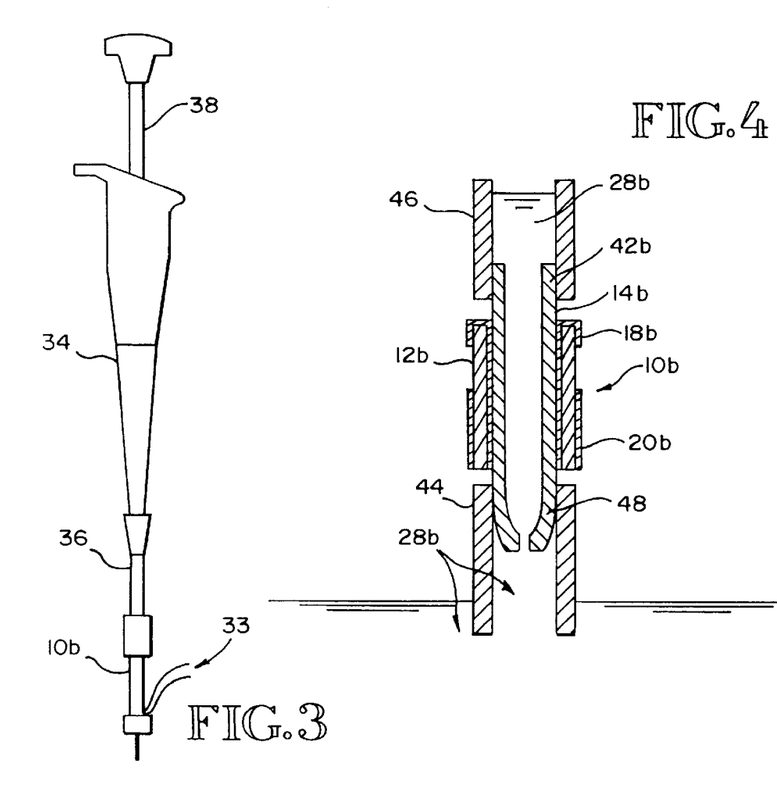
FIG. 3 is a manually operated piezoelectric pipette.
FIG. 4 is a cross-sectional view of piezoelectric pipette embodying further aspects of the present invention with a tube attached to the back end and another tube attached to the front end.

As also illustrated in FIG. 2, the piezoelectric pipette 10b can be mounted on a supporting mounting bracket arm 32. This arm can be attached to an automated robotic instrument which dips the device into the sample fluid 28b for aspirating and then moves it to another station for dispensing. Alternatively, the piezoelectric pipette 10b with wires 33 can be attached to a manual pipettor 34 having a disposable tip 36, as shown in FIG. 3. In this case the device is dipped into the sample fluid by a human operator and then manually moved to another container or substrate for dispensing. The plunger 38 of the manual pipettor can be used for priming, rinsing and emptying the device.

Figure 5:
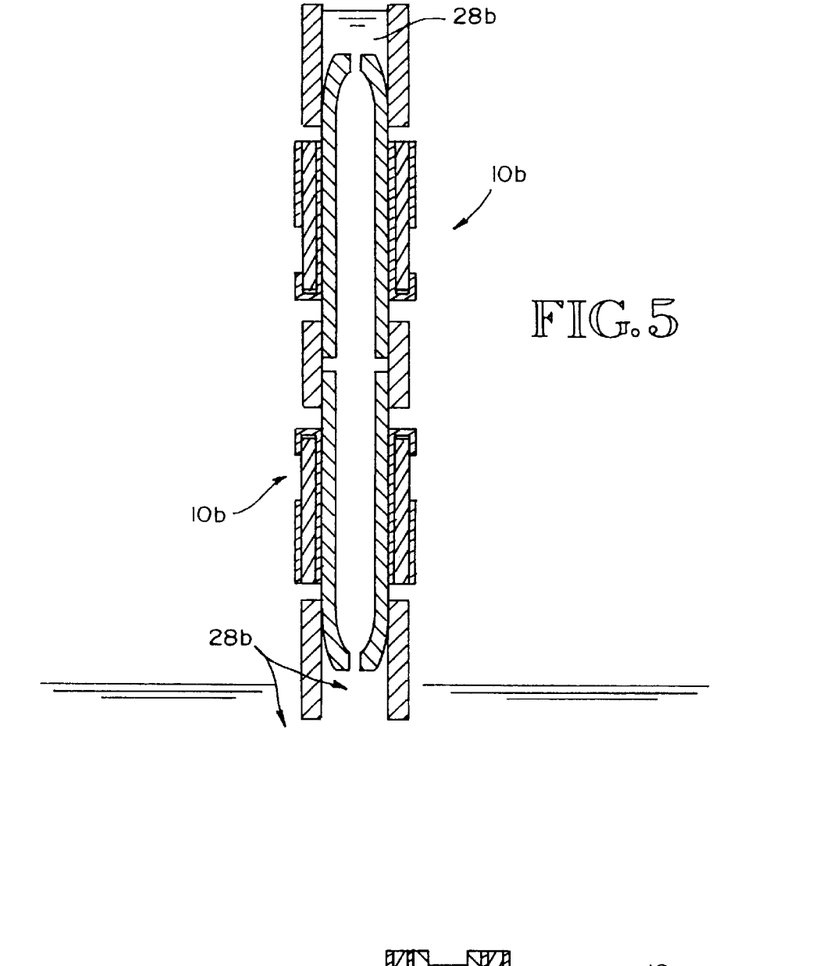
FIG. 5 is a cross-sectional view of two piezoelectric pipettes back-to-back forming a reversible continuous flow pump in accordance with the present invention.

Three different versions of the piezoelectric pipette 10b operating as a diffuser pump are shown in FIG. 2, FIG. 4 and FIG. 5. As seen in FIG. 2, attaching a reservoir 40 to the back end 42 of the piezoelectric pipette 10b allows larger volumes of fluid 28b to be drawn up. As seen in FIG. 4, by attaching tubing 44 and 46 to respective ends 48 and 42b respectively of pipette 10b, the piezoelectric pipette operates as a pump for a continuous flow system. A reversible continuous flow pump can be made by putting two piezoelectric pipettes 10b back to back as shown in FIG. 5. In each of the embodiments of FIGS. 2 and 4, the voltage source 19 of FIG. 1 may be used to apply an alternating current voltage across the inner and outer electrodes of the actuating piezoelectric elements. In the embodiment of FIG. 5, separate voltage sources may be used for the actuating electrodes or a single source may be selectively applied to one or the other of the actuating elements.

Integrated Sensor

Figure 6:
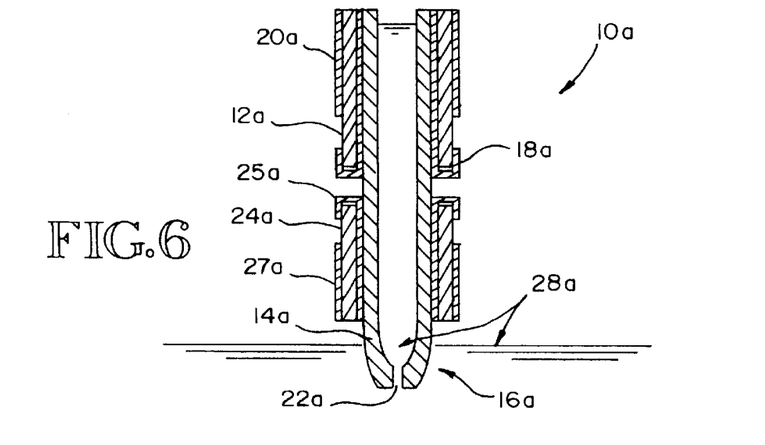
FIG. 6 is a cross-sectional view of piezoelectric pipette with a separate sensor embodying the present invention.
Figure 7:
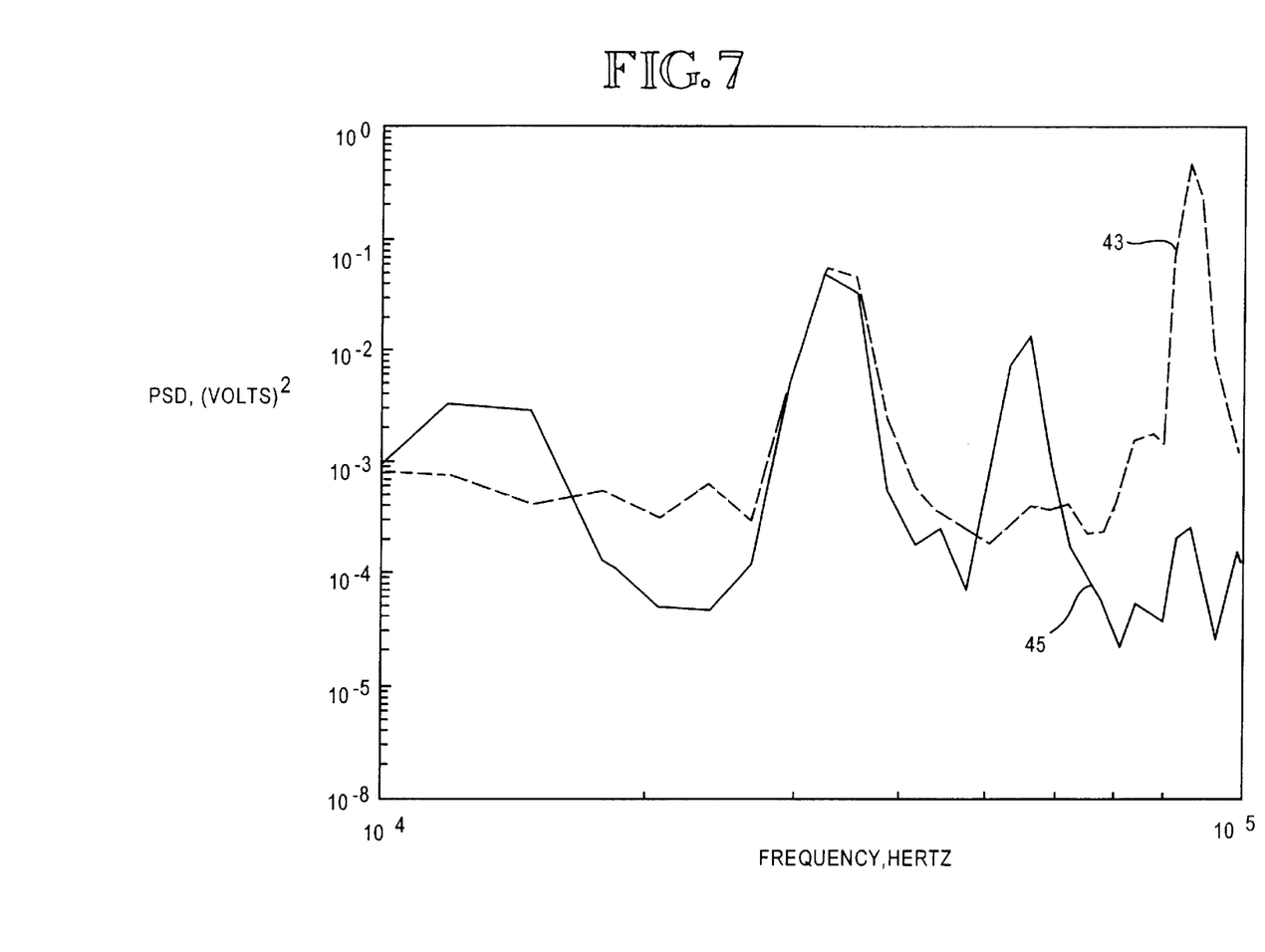
FIG. 7 is a graph of the power spectral densities of the sensors for water vs. Fluorinert fluids with the device operating in drop-on-demand mode illustrating a further aspect of the present invention.

The devices 10 and 10a shown in FIG. 1 and FIG. 6 respectively each incorporate a separate piezoelectric element 24 and 24a respectively which functions as a sensor to monitor the operational state of the device. The sensing elements 24 and 24a are proximal to their corresponding actuating elements 12 and 12a respectively with respect to the nozzles 22 and 22a. The sensor 24, 24a detects vibrations induced in the fluid 28, 28a, the glass capillary 14, 14a and the actuating piezoelectric element 12, 12a. By analyzing the voltage signal generated by this sensor across electrodes 25 and 27 and 25a and 27a it is possible to identify the operational state of the device, specifically, if the dispenser is operating properly both in drop-on-demand and diffuser pump modes of operation. Specifically it is possible to detect if the device is working properly, if it is empty or full when aspirating or dispensing, if the nozzle is partially or completely plugged when aspirating or dispensing, what type of fluid is being dispensed or if the device is trying to aspirate fluid from an empty container. The power spectral densities of the time signals are computed to make it easier to distinguish the differences between these various operating conditions. For example, FIG. 7 shows the power spectrial density (PSD) of the output from the sensor while the dispenser is dispensing in drop-on-demand mode. The PSDs in FIG. 7 were computed by averaging the fast Fourier transforms (FFTs) of 16 individual Hanning windowed data records of 128 points each sampled at a frequency of 375 KHz. The figure shows the difference in the sensor output if water 43 vs. Fluorinert 45 is being dispensed. At 90 KHz there is a difference of three orders of magnitude between the PSDs of water 43 and Fluorinert 45. Detection software will compare the PSDs at this frequency to determine if the sample fluid (water) or the working (Fluorinert) fluid is being dispensed.

Figure 8:
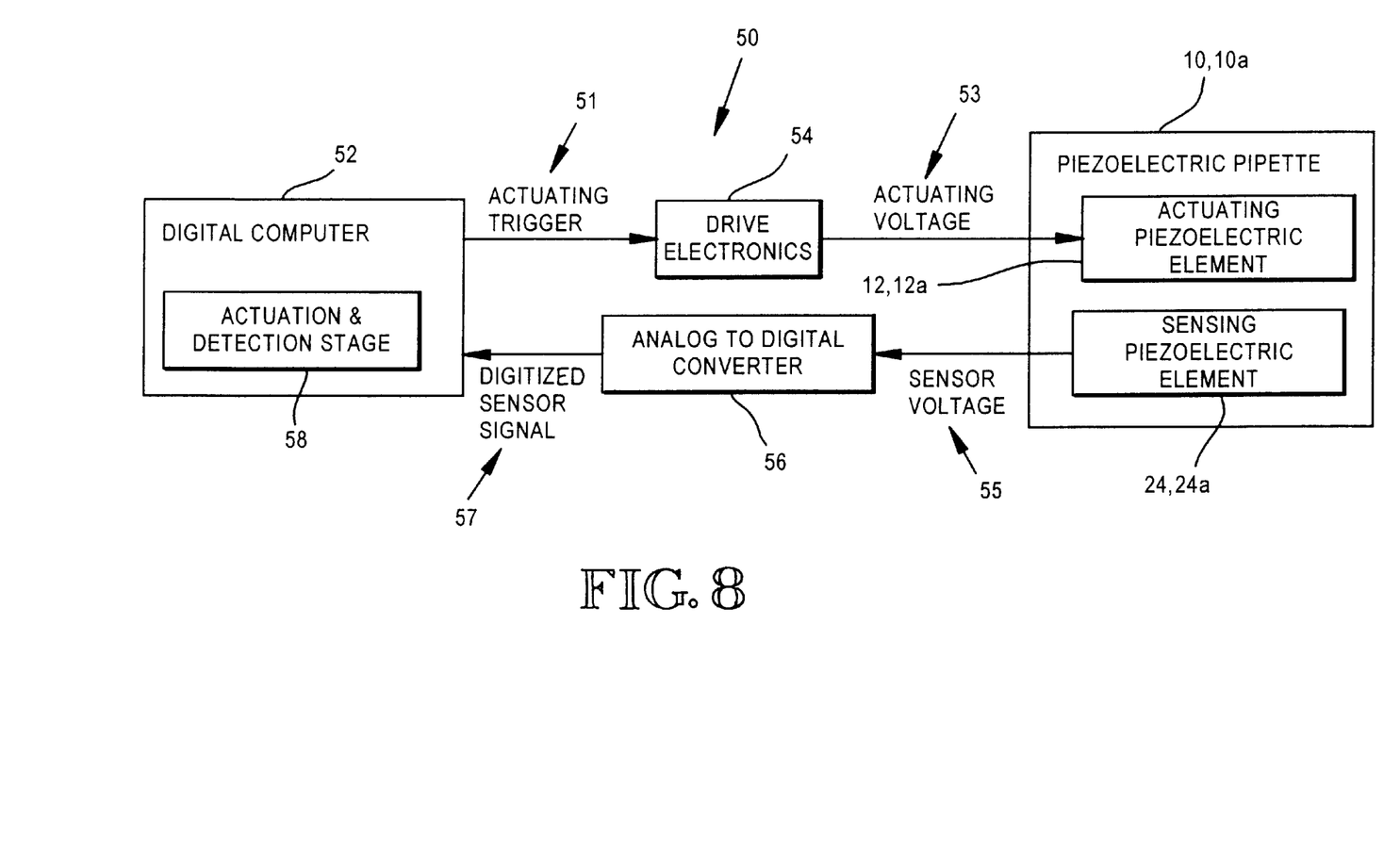
FIG. 8 is a block diagram of a dispenser actuation and sensor detection system embodying the present invention.
Figure 9:
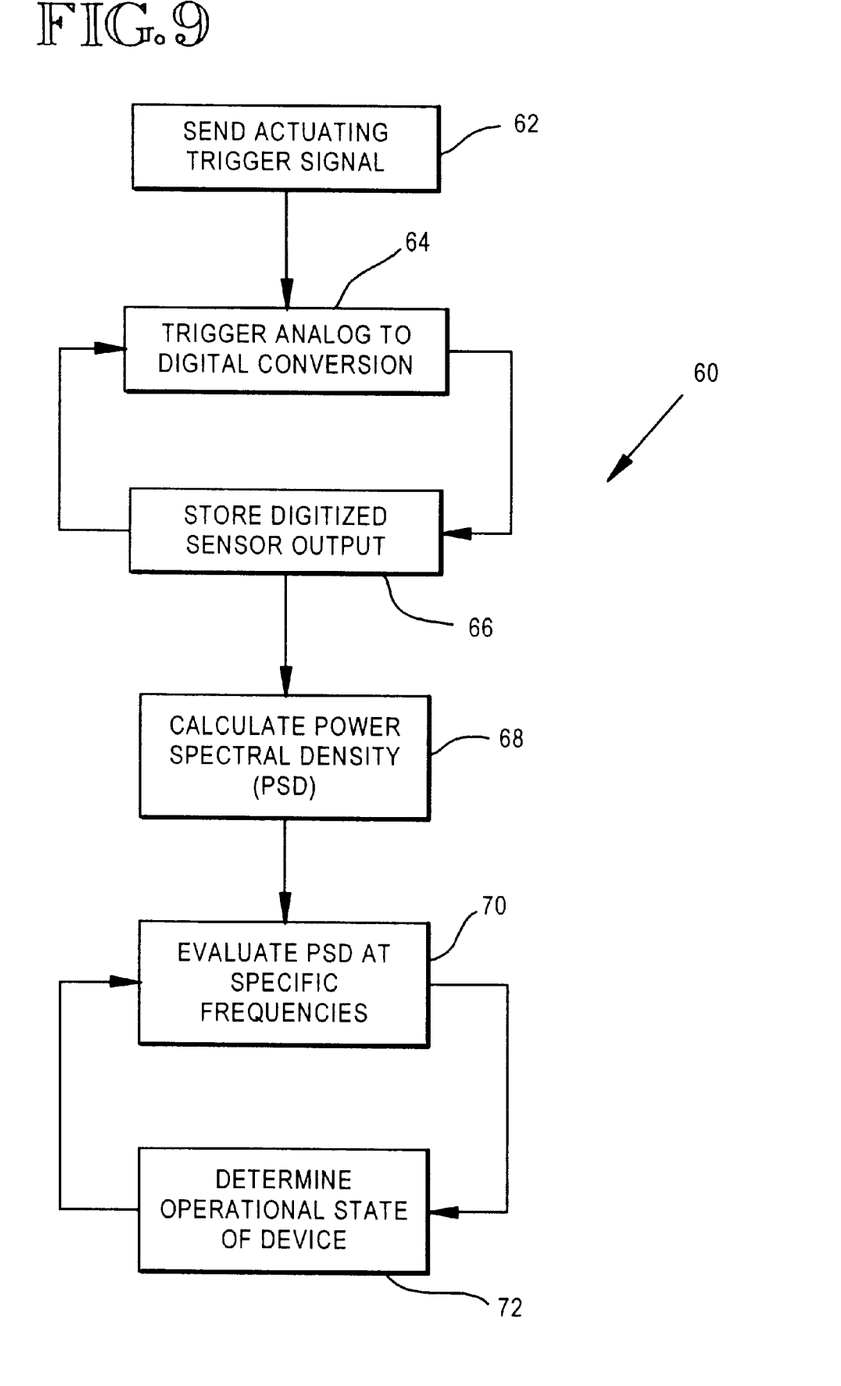
FIG. 9 is a flow diagram illustrating an actuation and detection method embodying the present invention.

A block diagram of the dispenser actuation and sensor detection system 50 is depicted in FIG. 8. It incorporates a digital computer 52, drive electronics 54 for the actuating piezoelectric element 12,12a, the piezoelectric pipette 10, 10a itself with an integrated sensor 24, 24a and an analog to digital converter (ADC) 56 for the sensor signal. The computer 52, upon implementing operating instructions in accordance with this embodiment of the present invention forms an actuation and detection stage 58. A flow diagram 60 of the actuation and detection stage operation is depicted in FIG. 9. First in step 62, an actuating trigger 51 command to actuate the device is issued to the drive electronics 54. The drive electronics 54 in turn generates an actuating voltage 53 to drive the actuating piezoelectric element 12, 12a with a voltage waveform. To obtain the sensor data, for FIG. 7 for example, the piezoelectric element may be driven with a 60 microsecond, 35 volt amplitude pulse. The voltage causes the actuating piezoelectric element to deflect which induces vibrations in the fluid, the glass capillary and the piezoelectric element itself. These vibrations are in turn converted to a sensor voltage signal 55 by the sensing piezoelectric element 24, 24a. The analog to digital converter (ADC) 56 is then, in step 64, triggered to sample and digitize this signal. The computer then in step 66 stores the digitized sensor signal 57 output values. Steps 64 and 66 are repeated. When the voltage signal is completely sampled, the data is made available for digital signal processing and analysis by the computer. The power spectral densities of FIG. 7 are then computed in step 68 using any accepted method of power spectral estimation. The PSD is then evaluated in step 70 by comparing the PSD value at different frequencies to known corresponding values for a particular operational state of the device. For each evaluation, the operational state of the device 10, 10a is determined in accordance with step 72. Steps 70 and 72 are repeated for all of the various operational states of the device.

Temperature Control

Figure 10:
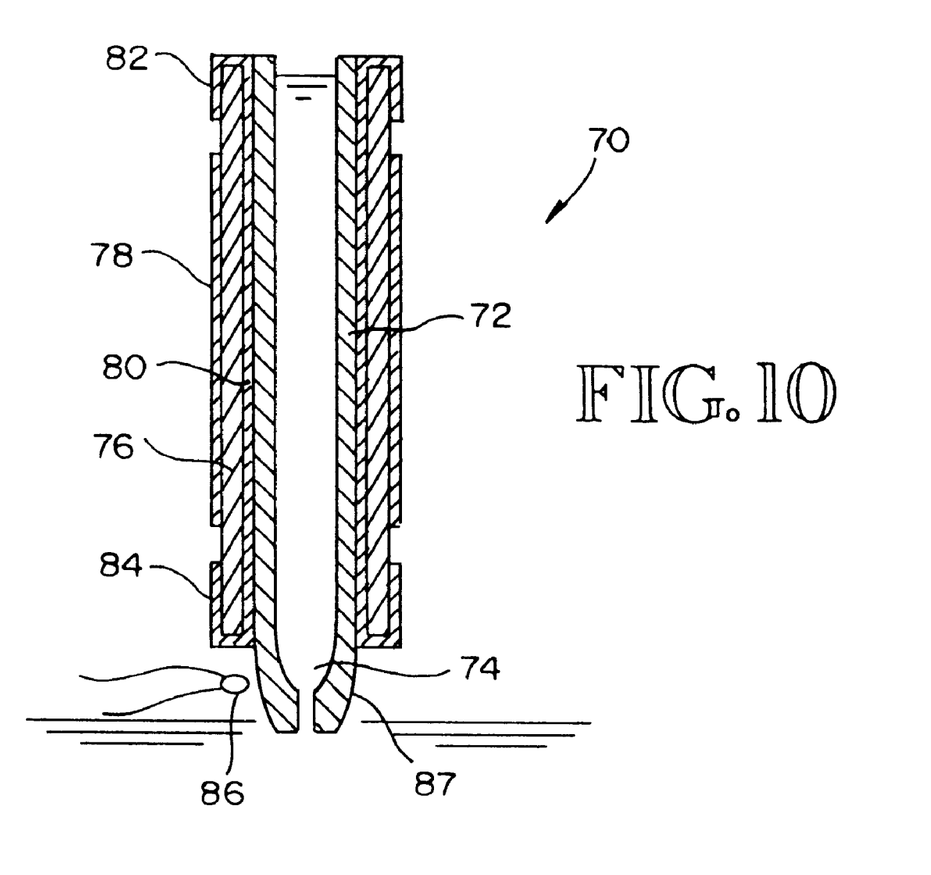
FIG. 10 is a cross-sectional view of a piezoelectric pipette with a thermocouple and heating system including an inner electrode functioning as an integrated heating element embodying the present invention.

FIG. 10 shows a piezoelectric pipette 70 wherein the temperature of the glass capillary 72 and thus the fluid 74 within the capillary may be controlled in accordance with a further aspect of the present invention. Here, the actuating element 76 is associated with an outer electrode 78 and an inner electrode 80 having two wrap-around electrode portions 82 and 84 on each end of the piezoelectric element 76. Applying a current between the wrap-around electrode portions 82 and 84 and thus through the inner electrode 80 causes the temperature of the device to increase. A thermocouple 86, depicted in FIG. 10, is closely adjacent the nozzle 87 and senses the temperature of the device. The temperature may be regulated with a temperature regulator 88 (FIG. 11) such as an Analog Devices AD594 as specified in the *Monolithic Thermocouple Amplifier Data Sheet* from Analog Devices. This integrated circuit controls the current passing through the inner electrode to maintain a set-point temperature using feedback from the thermocouple as depicted in the block diagram in FIG. 11.

Figure 11:
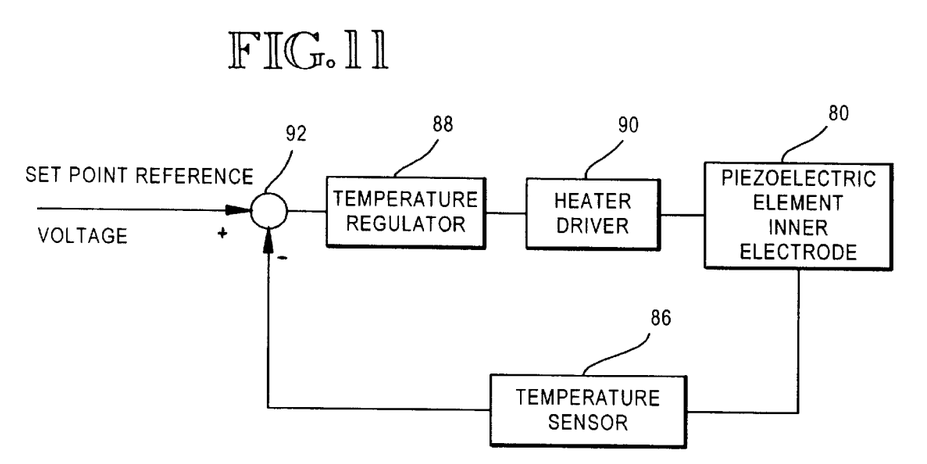
FIG. 11 is a block diagram of a temperature control system which may be employed with the pipette of FIG. 10 in accordance with the present invention.

As can be seen in FIG. 11, the temperature regulator 88 provides a control output to a heater driver 90 which applies the current to the inner electrode 80. The amount of current applied is dictated by the temperature regulator 88 and more specifically the difference between the output voltage of the thermocouple 86 and a set point reference voltage applied to a subtractor stage 92.

What is claimed is:

1. A diffuser pump comprising:
    a pipette including a capillary having a first end including a nozzle and a piezoelectric actuating element adjacent to the capillary; and
    an alternating current voltage source coupled across the piezoelectric actuating element and operable to generate and provide the alternating current voltage to the piezoelectric actuating element when the nozzle is immersed in a sample fluid;
    whereby with the nozzle immersed in a sample fluid, and the capillary at least partially filled with a working fluid, the alternating current voltage applied to the actuating element causes sample fluid to be drawn into the capillary.

2. A diffuser pump as defined in claim 1 wherein the alternating current voltage source provides alternating current voltage having one of a saw-tooth square-wave and sine-wave waveform.

3. A diffuser pump as defined in claim 1 wherein the capillary has a second end opposite the first end and wherein the diffuser pump further includes a reservoir attached to the second end of the capillary.

4. A diffuser pump comprising:
    a pipette including a capillary having a first end including a nozzle;
    a piezoelectric actuating element adjacent to the capillary;
    an alternating current voltage source coupled across the piezoelectric actuating element;
    wherein the capillary has a second end opposite the first end and wherein the diffuser pump further includes a first conduit attached to the first end and a second conduit attached to the second end whereby,
    with fluid filling the capillary and the conduits, the diffuser pump functions as a continuous flow pump.

5. A diffuser pump comprising
    a pipette including a capillary having a first end including a nozzle;
    a piezoelectric actuating element adjacent to the capillary;
    an alternating current voltage source coupled across the piezoelectric actuating element;
    wherein the capillary includes a second end opposite the first end, wherein the diffuser pump further includes a second pipette including a capillary having a first end including a nozzle and a second end opposite the first end and a piezoelectric actuating element adjacent the capillary, wherein the second ends of pipettes are attached for communicating with each other, and wherein the diffuser pump further includes conduit means attached to the first ends of the pipettes, whereby, with alternating current voltage selectively applied across the actuating elements, and with fluid filling the capillaries and conduits, the diffuser pump is arranged to function as a reversible continuous flow pump.

6. A diffuser pump as defined in claim 1 further including a mounting arm for disposing the nozzle immersed in a sample fluid.

7. A pipette sensing arrangement for sensing a working condition of a pipette, the arrangement comprising;
    a capillary having an end including a nozzle;
    a piezoelectric actuating element adjacent the capillary;
    first electrodes for applying electrical energy across the piezoelectric actuating element;
    a piezoelectric sensing element adjacent the capillary; and
    second electrodes for coupling the piezoelectric sensing element to a voltage sensor.

8. An arrangement as defined in claim 7 wherein the sensing element is proximal to the actuating element with reference to the nozzle.

9. An arrangement as defined in claim 7 wherein the voltage sensor includes an analog to digital converter for generating digital data responsive to the sensing element.

10. An arrangement as defined in claim 9 further including means for analyzing the digital data.

11. An arrangement as defined in claim 10 wherein the means for analyzing includes means for generating power spectral densities.

12. An arrangement as defined in claim 11 wherein the means for analyzing further includes comparing means for comparing the generated power spectral densities at preselected frequencies to predetermined power spectral density values corresponding to the preselected frequencies.

13. A temperature control arrangement for a pipette, the arrangement comprising;

a capillary having an end including a nozzle;

a piezoelectric actuating element adjacent the capillary; actuating electrodes for applying electrical energy across the piezoelectric actuating element, a current source for passing an electrical current through one of the actuating electrodes; and a temperature sensor closely adjacent the capillary for sensing the temperature of the capillary.

14. An arrangement as defined in claim 13 wherein the temperature sensor includes a thermocouple.

15. An arrangement as defined in claim 13 wherein the temperature sensor is closely adjacent the nozzle.

16. An arrangement as defined in claim 13 further including means for controlling the current source responsive to the temperature sensor.

17. An arrangement as defined in claim 16 wherein the temperature sensor includes means for generating a voltage representative of the sensed temperature and wherein the means for controlling is responsive to a difference between the voltage generated by the temperature sensor and a set point reference voltage.

18. An arrangement as defined in claim 13 wherein the actuating electrodes include an inner electrode between the actuating element and the capillary and an outer electrode adjacent the actuating element on a side of the actuating element opposite the capillary, and wherein the current source is coupled to the inner electrode for passing the electrical current through the inner electrode.

19. A method of using a piezoelectric pipetting device including a capillary having a first end including a nozzle and a piezoelectric actuating element adjacent to the capillary; and an alternating current voltage source coupled across the piezoelectric actuating element and operable to generate and provide the alternating current voltage to the piezoelectric actuating element, the method including the steps of:

(a) inserting the nozzle into a sample fluid;

(b) providing the alternating current voltage to the piezoelectric actuating element; and (c) drawing sample fluid into the capillary.

20. The method of claim 19 wherein the inserting step is performed by an automatic robotic instrument coupled to the device.

21. The method of claim 19 including the further steps of:

(d) withdrawing the nozzle from the sample fluid;

(e) supplying an alternating current voltage to the piezoelectric actuating; and (f) dispensing the sample fluid from the nozzle.

22. The method of claim 21 wherein the withdrawing step is performed by an automatic robotic instrument coupled to the device.

* * * * *